US012569294B2

(12) United States Patent (10) Patent No.: US 12,569,294 B2

Harmouche et al. (45) Date of Patent: Mar. 10, 2026

(54) TIMING SYSTEM FOR USE DURING ABLATION PROCEDURE

(71) Applicant: Boston Scientific Scimed, Inc., Maple Grove, MN (US)

(72) Inventors: Chadi Harmouche, Quebec (CA); Keegan Harper, Encinitas, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1499 days.

(21) Appl. No.: 16/190,726

(22) Filed: Nov. 14, 2018

(65) Prior Publication Data

US 2019/0142509 A1 May 16, 2019

Related U.S. Application Data

(60) Provisional application No. 62/607,045, filed on Dec. 18, 2017, provisional application No. 62/586,080, filed on Nov. 14, 2017.

(51) Int. Cl.
A61B 18/14 (2006.01)
A61B 5/00 (2006.01)
(Continued)

(52) U.S. Cl.
CPC ........ A61B 18/1492 (2013.01); A61B 5/4836 (2013.01); A61B 18/02 (2013.01);
(Continued)

(58) Field of Classification Search
CPC ............ A61B 18/1492; A61B 18/1233; A61B 2018/00375; A61B 2018/00577;
(Continued)

(56) References Cited

U.S. PATENT DOCUMENTS

| | | | |
|---|---|---|---|
| 2012/0123400 A1 | 5/2012 | Francischelli et al. | |
| 2014/0163543 A1* | 6/2014 | Allison ............. | A61B 18/1492 |
| | | | 606/33 |
| 2017/0290618 A1* | 10/2017 | Lalonde ................ | A61B 18/02 |

FOREIGN PATENT DOCUMENTS

| | | |
|---|---|---|
| CN | 101316560 A | 12/2008 |

OTHER PUBLICATIONS

International Search Report and Written Opinion issued in PCT/US2018/060975, mailed Feb. 28, 2019, 10 pages.

(Continued)

*Primary Examiner* — Joanne M Rodden
*Assistant Examiner* — Bo Ouyang
(74) *Attorney, Agent, or Firm* — Nelson Mullins Riley & Scarborough LLP

(57) ABSTRACT

A timing system during an ablation procedure having a time to isolation includes an automated timer that receives a first time setting. The first time setting provides a maximum time that the ablation procedure can continue without reaching the time to isolation. A catheter system including the timing system can also include a control system that is configured to automatically stop the ablation procedure if the first time setting expires without reaching the time to isolation. The operator can input the first time setting via a graphical display of the catheter system. The automated timer can generate an expiration signal if the first time setting expires without reaching the time to isolation. The automated timer can further receive a second time setting from the operator that provides a maximum time that the ablation procedure can continue after reaching the time to isolation.

8 Claims, 6 Drawing Sheets

(51) Int. Cl.
 *A61B 18/02*    (2006.01)
 *A61B 17/00*    (2006.01)
 *A61B 18/00*    (2006.01)
 *A61B 18/12*    (2006.01)

(52) U.S. Cl.
 CPC ............... *A61B 2017/00084* (2013.01); *A61B 2018/00375* (2013.01); *A61B 2018/00577* (2013.01); *A61B 2018/00642* (2013.01); *A61B 2018/00732* (2013.01); *A61B 2018/00761* (2013.01); *A61B 2018/00791* (2013.01); *A61B 2018/00839* (2013.01); *A61B 2018/00886* (2013.01); *A61B 2018/00898* (2013.01); *A61B 2018/00904* (2013.01); *A61B 2018/0212* (2013.01); *A61B 18/1233* (2013.01)

(58) Field of Classification Search
 CPC A61B 2018/00642; A61B 2018/00839; A61B 2018/00886; A61B 2018/00898; A61B 2018/00904; A61B 2018/0212; A61B 2017/00084; A61B 5/4836; A61B 2018/00732; A61B 2018/00761; A61B 2018/00791
 See application file for complete search history.

(56)    References Cited

OTHER PUBLICATIONS

Communication pursuant to Article 94(3) EPC for EPO application No. 18779532.3 dated Mar. 28, 2023. 6 pages.

\* cited by examiner

TIMING SYSTEM FOR USE DURING ABLATION PROCEDURE

RELATED APPLICATIONS

This application claims the benefit of U.S. Provisional Application No. 62/586,080, filed on Nov. 14, 2017, and entitled "TIMING SYSTEM FOR USE WITH ABLATION PROCEDURE," and U.S. Provisional Application No. 62/607,405, filed on Dec. 18, 2017 and entitled "TIMING SYSTEM FOR USE WITH ABLATION PROCEDURE." As far as permitted, the contents of U.S. Provisional Application Nos. 62/586,080 and 62/607,405 are incorporated in their entirety herein by reference.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (i.e. farthest from the user or operator) portion of the catheter, and often at the tip of the catheter.

Various forms of energy can be used to ablate diseased heart tissue. These can include cryoablation procedures which use cryogenic fluid within cryoballoons (also sometimes referred to herein as "cryogenic balloons" or "balloon catheters"), radio frequency (RF), ultrasound and laser energy, to name a few. During a cryoablation procedure, with the aid of a guide wire, the distal tip of the catheter is positioned adjacent to targeted cardiac tissue, at which time energy is delivered to create tissue necrosis, rendering the ablated tissue incapable of conducting electrical signals. The dose of energy delivered is a critical factor in increasing the likelihood that the treated tissue is permanently incapable of conduction. At the same time, delicate collateral tissue, such as the esophagus, the bronchus, and the phrenic nerve surrounding the ablation zone can be damaged and can lead to undesired complications. Thus, the operator must finely balance delivering therapeutic levels of energy to achieve intended tissue necrosis while avoiding excessive energy leading to collateral tissue injury.

Atrial fibrillation (AF) is one of the most common arrhythmias treated using catheter ablation. AF is typically treated by pulmonary vein isolation, a procedure that removes unusual electrical conductivity in the pulmonary vein. In the earliest stages of the disease, paroxysmal AF, the treatment strategy involves isolating the pulmonary veins from the left atrial chamber. Cryoballoon ablation procedures to treat atrial fibrillation have increased in use in the last several years. In part, this stems from the ease of use, shorter procedure times and improved patient outcomes that are possible through the use of cryoballoon ablation procedures. Despite these advantages, there remains needed improvement to further improve patient outcomes and to better facilitate real-time physiological monitoring of tissue to optimally titrate energy to perform both reversible "ice mapping" and permanent tissue ablation.

The objective of any device for the treatment of AF is to achieve isolation in all, not just some, of the pulmonary veins. Also, it is understood that complete occlusion of each pulmonary vein with the cryogenic balloon is required for adequate antral ablation and electrical isolation. Without pulmonary vein occlusion, blood flow over the balloon during ablation decreases the likelihood of sufficient lesion formation.

Often times during catheter ablation procedures, the operator may use timers to determine the length of time that ablative energy is being delivered to the tissue. Typically, such timers are simply used for purposes of keeping track of how much time has elapsed during various stages of the procedure. For example, the operator can look at the timer and see that ablative energy has been delivered to the targeted tissue for a specific amount of time. Unfortunately, the use of timers in such a manner has not always been sufficient as a means to effectively reduce total energy delivery and potential collateral tissue damage during the catheter ablation procedure.

SUMMARY

The present invention is directed toward a timing system during an ablation procedure, the ablation procedure including a time to isolation, i.e. the moment when cardiac electrical signals during an ablation procedure are lost or "isolated" due to tissue ablation. In various embodiments, the timing system includes an automated timer that is configured to receive a first time setting from the operator. The first time setting provides a maximum time that the ablation procedure can continue without reaching the time to isolation.

Additionally, the present invention is further directed toward a catheter system including the timing system as described above, and a control system that is configured to automatically stop the ablation procedure if the first time setting expires without reaching the time to isolation. The catheter system can further include a graphical display that is electrically coupled to the timing system and the control system, wherein the operator inputs the first time setting via the graphical display. The automated timer can generate an expiration signal if the first time setting expires without reaching the time to isolation. Additionally, the automated timer can transmit the expiration signal to the graphical display, and the graphical display can notify the operator in one of a visual or audio manner that the expiration signal has been generated.

In certain embodiments of the timing system, the automated timer is further configured to receive a second time setting from the operator. The second time setting provides a maximum time that the ablation procedure can continue after reaching the time to isolation. In some such embodiments, the automated timer automatically switches from the first time setting to the second time setting upon reaching the time to isolation prior to the expiration of the first time setting.

Further, the present invention is also directed toward a catheter system including the timing system as described above in the preceding paragraph, and a control system that is configured to automatically stop the ablation procedure when the second time setting expires after reaching the time to isolation. The catheter system can further include a graphical display that is electrically coupled to the timing system and the control system, wherein the operator inputs the first time setting and the second time setting via the graphical display. Additionally, the automated timer can generate an expiration signal when the second time setting expires after reaching the time to isolation. Further, the automated timer can transmit the expiration signal to the graphical display, and the graphical display can subsequently notify the operator in one of a visual or audio manner that the expiration signal has been generated.

Moreover, in some embodiments of the timing system, the automated timer is further configured to receive a third time setting and a fourth time setting from the operator. The third time setting provides a thaw time after the expiration of the second time setting, and the fourth time setting provides a maximum time that a second ablation procedure can continue after expiration of the third time setting.

Still further, the present invention is also directed toward a catheter system including the timing system as described above in the previous paragraph, and a control system that is configured to automatically stop the second ablation procedure when the fourth time setting expires. The catheter system can further include a graphical display that is electrically coupled to the timing system and the control system, wherein the operator inputs the first time setting, the second time setting, the third time setting and the fourth time setting via the graphical display. The automated timer generates an expiration signal when the fourth time setting expires. Additionally, the automated timer can transmit the expiration signal to the graphical display, and the graphical display can subsequently notify the operator in one of a visual or audio manner that the expiration signal has been generated.

The present invention is further directed toward a timing system during an ablation procedure, the ablation procedure including a time to isolation, the timing system including an automated timer that is configured to receive a first time setting from the operator, the first time setting providing a maximum time that the ablation procedure can continue after reaching the time to isolation.

Additionally, the present invention is further directed toward a method for controlling timing during an ablation procedure, the ablation procedure including a time to isolation, the method including receiving a first time setting from the operator with an automated timer, the first time setting providing a maximum time that the ablation procedure can continue without reaching the time to isolation.

Further, the present invention is also directed toward a method for controlling timing during an ablation procedure, the ablation procedure including a time to isolation, the method including receiving a first time setting from the operator with an automated timer, the first time setting providing a maximum time that the ablation procedure can continue after reaching the time to isolation.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Embodiments of the present invention are described herein in the context of a timing system that is usable within a catheter system, e.g., an intravascular catheter system such as a cryogenic balloon catheter system, during an ablation procedure. More particularly, as provided in detail herein, the timing system can be an automated system that allows a health care professional or "operator" to use their own specific timing parameters during the ablation procedure so as to assist the operator in more easily and precisely controlling the timing of various stages of the ablation procedure. This further enables the operator to more effectively minimize total energy delivery and potential collateral tissue damage.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound and laser energy, as non-exclusive examples. The present invention is intended to be effective with any or all of these and other forms of energy.

Figure 1:
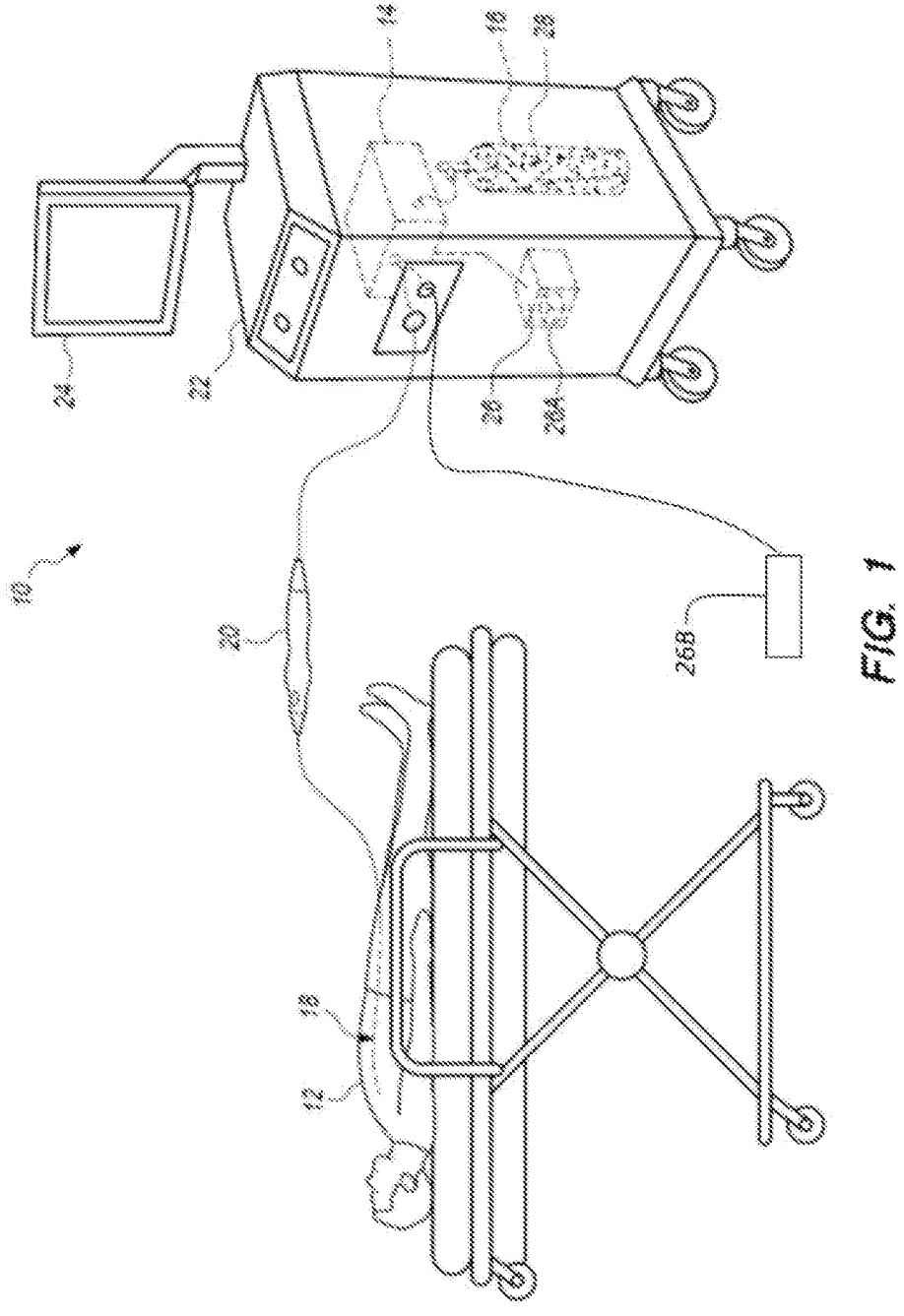
FIG. 1 is a simplified schematic side view illustration of a patient and an embodiment of an intravascular catheter system having features of the present invention, the intravascular catheter system including a timing system.

FIG. 1 is a simplified schematic side view illustration of an embodiment of a medical device 10 for use with a patient 12, which can be a human being or an animal. Although the specific medical device 10 illustrated and described herein pertains to and refers to an intravascular catheter system 10 such as a cryogenic balloon catheter system, it is understood and appreciated that other types of medical devices 10 or systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of an intravascular catheter system is not intended to be limiting in any manner.

The design of the intravascular catheter system 10 can be varied. In certain embodiments, such as the embodiment illustrated in FIG. 1, the intravascular catheter system 10 can include one or more of a control system 14 (illustrated in phantom), a fluid source 16 (illustrated in phantom), a balloon catheter 18, a handle assembly 20, a control console 22, a graphical display 24, and a timing system 26.

It is understood that although FIG. 1 illustrates the structures of the intravascular catheter system 10 in a particular position, sequence and/or order, these structures can be located in any suitably different position, sequence and/or order than that illustrated in FIG. 1. It is also understood that the intravascular catheter system 10 can include fewer or additional components than those specifically illustrated and described herein.

In various embodiments, the control system 14 is configured to monitor and control various processes of the ablation procedure. More specifically, the control system 14 can monitor and control release and/or retrieval of a cooling fluid 28 (e.g., a cryogenic fluid) to and/or from the balloon catheter 18. The control system 14 can also control various structures that are responsible for maintaining and/or adjusting a flow rate and/or pressure of the cryogenic fluid 28 that is released to the balloon catheter 18 during the cryoablation procedure. In such embodiments, the intravascular catheter system 10 delivers ablative energy in the form of cryogenic fluid 28 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive data and/or other information (hereinafter sometimes referred to as "sensor output") from various structures within the intravascular catheter system 10. Additionally, as provided in greater detail herein below, the control system 14 can further receive data and/or timing information (hereinafter sometimes referred to as "timing output") from the timing system 26 during an ablation procedure.

In some embodiments, the control system 14 can receive, monitor, assimilate and/or integrate the sensor output, the timing output and/or any other data or information received from any structure within the intravascular catheter system 10 in order to control the operation of the balloon catheter 18. As provided herein, in various embodiments, the control system 14 can initiate and/or terminate the flow of cryogenic fluid 28 to the balloon catheter 18 based on the sensor output and/or the timing output. Still further, or in the alternative, the control system 14 can control positioning of portions of the balloon catheter 18 within the body of the patient 12, and/or can control any other suitable functions of the balloon catheter 18.

The fluid source 16 contains the cryogenic fluid 28, which is delivered to the balloon catheter 18 with or without input from the control system 14 during a cryoablation procedure. Once the ablation procedure has initiated, the cryogenic fluid 28 can be delivered to the balloon catheter 18 and the resulting gas, after a phase change, can be retrieved from the balloon catheter 18, and can either be vented or otherwise discarded as exhaust. Additionally, the type of cryogenic fluid 28 that is used during the cryoablation procedure can vary. In one non-exclusive embodiment, the cryogenic fluid 28 can include liquid nitrous oxide. However, any other suitable cryogenic fluid 28 can be used. For example, in one non-exclusive alternative embodiment, the cryogenic fluid 28 can include liquid nitrogen.

The design of the balloon catheter 18 can be varied to suit the specific design requirements of the intravascular catheter system 10. As shown, the balloon catheter 18 is configured to be inserted into the body of the patient 12 during the cryoablation procedure, i.e. during use of the intravascular catheter system 10. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a user. As used herein, a user can include a physician, a physician's assistant, a nurse and/or any other suitable person and/or individual. In certain embodiments, the balloon catheter 18 is positioned within the body of the patient 12 utilizing at least a portion of the sensor output that is received by the control system 14. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue (not shown). While specific reference is made herein to the balloon catheter 18, as noted above, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the intravascular catheter system 10. In the embodiment illustrated in FIG. 1, the handle assembly 20 is separate from, but in electrical and/or fluid communication with the control system 14, the fluid source 16 and/or the graphical display 24. In some embodiments, the handle assembly 20 can integrate and/or include at least a portion of the control system 14 within an interior of the handle assembly 20. It is understood that the handle assembly 20 can include fewer or additional components than those specifically illustrated and described herein.

In various embodiments, the handle assembly 20 can be used by the operator to initiate and/or terminate the cryoablation process, e.g., to start the flow of the cryogenic fluid 28 to the balloon catheter 18 in order to ablate certain targeted heart tissue of the patient 12. In certain embodiments, the control system 14 can override use of the handle assembly 20 by the operator. Stated in another manner, in some embodiments, based at least in part on the sensor output and/or the timing output, the control system 14 can terminate the cryoablation process without the operator using the handle assembly 20 to do so.

The control console 22 is coupled to the balloon catheter 18 and the handle assembly 20. Additionally, in the embodiment illustrated in FIG. 1, the control console 22 includes at least a portion of the control system 14, the fluid source 16, the graphical display 24, and the timing system 26. However, in alternative embodiments, the control console 22 can contain additional structures not shown or described herein. Still alternatively, the control console 22 may not include various structures that are illustrated within the control console 22 in FIG. 1. For example, in certain non-exclusive alternative embodiments, the control console 22 does not include the graphical display 24.

In various embodiments, the graphical display 24 is electrically connected to the control system 14 and the timing system 26. Additionally, the graphical display 24 provides the operator of the intravascular catheter system 10 with information that can be used before, during and after the cryoablation procedure. For example, the graphical display 24 can provide the operator with information based on the sensor output, the timing output, and any other relevant information that can be used before, during and after the cryoablation procedure. The specifics of the graphical display 24 can vary depending upon the design requirements of the intravascular catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time, e.g., during an ablation procedure. Further, in various embodiments, the graphical display 24 can include one or more colors, different sizes, varying brightness, etc., that may act as alerts to the operator. Additionally, or in the alternative, the graphical display 24 can provide audio data or information to the operator.

The timing system 26 provides the operator with a mechanism, i.e. an automated timer 26A, by which the operator can utilize their own specific timing parameters to more easily and precisely control the timing of the various stages of the cryoablation procedure. For example, in certain embodiments, the timing system 26 can be used in conjunction with the graphical display 24 and the control system 14 to effectively control the timing of the various stages of the cryoablation procedure based upon time to effect. As utilized herein, the "time to effect" refers to the moment when cardiac electrical signals during an ablation procedure are lost or "isolated" due to tissue ablation. Thus, the time to effect can also be referred to in some instances as the "time to isolation". It is appreciated that the time to effect or time to isolation is a variable that is determined only through the process of an ablation procedure, and may not actually be achieved in any given ablation procedure. As such, although the ablation procedure can be said to include a time to isolation, it is understood that the specific time to isolation for any given ablation procedure is actually unknown and only a potentiality until it happens (if it does at all) during the ablation procedure.

One representative example of time to effect or time to isolation would be when signals from the left atrium no longer appear in the pulmonary vein due to a circumferential lesion.

Alternatively, in other embodiments, the timing system 26 can be used to effectively control the timing of the various stages of the cryoablation procedure based upon factors other than the time to isolation.

The timing system 26 and/or the automated timer 26A can be electrically connected to the control system 14 and the graphical display 24. As such, any timing output that is provided by the timing system 26 can be used by the control system 14 to control the operation of the various features and components of the intravascular catheter system 10. Additionally, any timing output and any information and data that is based on the timing output can be displayed visually and/or in audio format on the graphical display 24.

As provided herein, the timing system 26 and/or the automated timer 26A can be configured to set or control the amount of time that the ablation procedure can be continued before and/or after the recognition of the time to isolation. For example, in one embodiment, the automated timer 26A can be utilized as a pre-isolation timer. Stated in another manner, the operator can input a first (pre-isolation) time setting into the automated timer 26A. During use as a pre-isolation timer, the operator can set the automated timer 26A to define a maximum time, e.g., ninety seconds, where the ablation procedure can be continued without having detected electrical isolation. In the event that the established maximum time for the automated timer 26A when used as a pre-isolation timer runs out, i.e. the first (pre-isolation) time setting expires, without having detected electrical isolation, the control system 14 can be configured to automatically shut down or stop the ablation procedure at that point. By placing a limit on the amount of time that ablative energy can be delivered to the tissue without achieving the time to isolation prior to shutting down the ablation procedure, the intravascular catheter system 10 can more effectively minimize potential collateral tissue damage. It is appreciated that the maximum time for the automated timer 26A when used as a pre-isolation timer can be set at any suitable time based on the knowledge and experience of the operator. For example, in certain non-exclusive alternative embodiments, the maximum time for the automated timer 26A when used as a pre-isolation timer (the first (pre-isolation) time setting) can be set at anywhere from approximately sixty seconds to approximately one hundred twenty seconds. In other non-exclusive alternative embodiments, the maximum time for the automated timer 26A when used as a pre-isolation timer can be set at anywhere from approximately seventy-five seconds to approximately one hundred five seconds. Still alternatively, the operator can choose another suitable time for the maximum time for the automated timer 26A when used as a pre-isolation timer.

In certain embodiments, the timing system 26 can be configured to provide audio and/or visual notification to the operator via the graphical display 24 when time to isolation has been achieved. More specifically, the timing system 26 can generate a signal (i.e. an isolation signal) when time to isolation has been achieved in order to provide proper notification to the operator. Further, in some embodiments, the timing system 26 can be configured to provide audio and/or visual notification to the operator via the graphical display 24 when the first (pre-isolation) time setting has expired. More specifically, the timing system 26 can generate a signal (i.e. an expiration signal) when the first (pre-isolation) time setting has expired prior to achieving time to isolation in order to provide proper notification to the operator.

Additionally, or in the alternative, the timing system 26 and/or the automated timer 26A can also be utilized as a post-isolation timer. Stated in another manner, the operator can input a second (post-isolation) time setting into the automated timer 26A. More specifically, in such embodiments, the timing system 26 enables the operator to set the ablation duration after the system detects electrical isolation. It is appreciated that the time when the system effectively detects electrical isolation can either be entered manually by the operator (with a button for example) at an appropriate time during the ablation procedure, or can be detected automatically by the control console 22 or control system 14 through an algorithm. Once electrical isolation is so detected, the timing system 26 can be utilized such that the ablation procedure will continue for a time equal to the specific time that has been preset by the operator, i.e. equal to the second (post-isolation) time setting. Subsequently, upon reaching the expiration of the second (post-isolation) time setting, the control system 14 can be configured to automatically shut down or stop the ablation procedure at that point. In certain applications, the specific time set be the operator for the post-isolation timer can be dependent upon the time it took to achieve electrical isolation.

For example, in certain non-exclusive alternative embodiments, the maximum time for the automated timer 26A when used as a post-isolation timer, i.e. the second (post-isolation) time setting, can be set at anywhere from approximately ninety seconds to approximately one hundred fifty seconds. In other non-exclusive alternative embodiments, the maximum time for the automated timer 26A when used as a post-isolation timer can be set at anywhere from approximately one hundred twenty seconds to approximately one hundred eighty seconds. Still alternatively, the operator can choose any other suitable time for the maximum time for the automated timer 26A when used as a post-isolation timer.

In some embodiments, the timing system 26 can be configured to provide audio and/or visual notification to the operator via the graphical display 24 when the second (post-isolation) time setting has expired. More specifically, the timing system 26 can generate a signal (i.e. an expiration signal) when the second (post-isolation) time setting has expired after achieving time to isolation in order to provide proper notification to the operator.

Thus, as provided herein, in various embodiments, the operator can selectively input one or more of a first (pre-isolation) time setting and a second (post-isolation) time setting into the timing system 26 for use during an ablation procedure. In some such embodiments, the time settings input by the operator can be input via the graphical display 24. Additionally, based on the specific disclosure provided herein, the control system 14 is able to control the operation of the intravascular catheter system 10 during an ablation procedure based at least in part on the timing output that is received from the timing system 26.

Additionally, as shown, the timing system 26 can further include a timing activator 26B that can be used to start and/or stop the automated timers 26A as desired. In one non-exclusive embodiment, the timing activator 26B can be provided in the form of a foot switch that can be accessed by the operator during the ablation procedure. Further, or in the alternative, in another non-exclusive embodiment, the timing activator 26B can be provided in the form of a button that is accessible through the graphic display 24. Still alternatively, the timing activator 26B can be provided in another suitable form for use by the operator.

As part of the ablation procedure, the timing activator 26B can be utilized for purposes of starting the automated timer 26A at the beginning of the ablation procedure. Subsequently, the timing activator 26B can also be utilized for stopping the automated timer 26A when the time to effect or time to isolation has been effectively reached. Stated in another manner, with such design, the automated timer is configured to monitor elapsed time during the ablation procedure until the time to isolation is achieved for the targeted tissue.

In one embodiment, the operator can utilize the timing activator 26B to manually indicate when the targeted tissue has been effectively isolated or is no longer conducting electrical signals based on certain mapping signals or other appropriate indicators. In such embodiment, the timing system 26, i.e. the timing activator 26B, is utilized by the operator to start the automated timer 26A at the beginning of the ablation procedure, and to stop the automated timer 26A when the operator indicates that the targeted tissue is effectively isolated and non-conducting, i.e. at the time to effect.

Further, as provided herein, the control system 14 can receive data and/or timing information (hereinafter sometimes referred to as "timing output") from the timing system 26. Additionally, or in the alternative, the control system 14 can also receive data and/or other information (hereinafter sometimes referred to as "sensor output") from various structures within the cryogenic balloon catheter system 10. For example, in certain embodiments, the timing system 26 can include and/or incorporate the use of one or more sensors that can be utilized to ensure the proper positioning, use and effect of the balloon catheter 18 during the ablation procedure. Additionally, with such design, the sensors can provide the desired sensor output to the control system 14.

In some embodiments, the control system 14 can assimilate and/or integrate the timing output, the sensor output, and/or any other data or information received from any structure within the cryogenic balloon catheter system 10 in order to control the operation of the balloon catheter 18. Still further, or in the alternative, the control system 14 can control positioning of portions of the balloon catheter 18 within the body of the patient 12, and/or can control any other suitable functions of the balloon catheter 18.

In another embodiment, the timing system 26 can be configured to automatically detect tissue isolation, and thus the time to effect, through mapping signals or other suitable indicators, e.g., that can be sensed with the sensors. Stated in another manner, in such embodiment, the sensors can be specifically configured to sense or detect electrical signals, or the lack thereof, that are emanating from the targeted cardiac tissue. As such, the sensors are configured to provide sensor output to the control system 14 and the graphical display 24 related to whether or not the targeted cardiac tissue is still conducting electrical signals. Thus, it is appreciated that the time when the system effectively detects electrical isolation can either be entered manually by the operator (with a button for example) at an appropriate time during the ablation procedure, or can be detected automatically by the sensors, control console 22 or control system 14 through an algorithm.

The sensors can be positioned within the cryogenic balloon catheter system 10 in any suitable manner. For example, the sensors can be positioned within the control console 22. Additionally, or in the alternative, the sensors can be positioned in another suitable position within the cryogenic balloon catheter system 10. For example, in certain embodiments, sensors can be positioned within the control system 14, within the handle assembly 20, adjacent to or on the balloon catheter 18 (i.e. such that the sensors can be positioned within the patient during the ablation procedure), or in another suitable location.

Additionally, the sensors have any suitable design. For example, in certain non-exclusive embodiments, the sensors can include an electrical detection sensor (e.g., electrodes that can be positioned near the targeted cardiac tissue), a pressure sensor, a temperature sensor, or another suitable type of sensor. In various embodiments, the sensors can include electrodes mounted on or otherwise integrated into the balloon catheter 18.

As noted, in certain embodiments, the timing system 26 can be configured to provide audio and/or visual notification to the operator via the graphical display 24 when time to isolation has been achieved. More specifically, the timing system 26 can generate a signal (i.e. an isolation signal) or alert when time to isolation has been achieved in order to provide proper notification to the operator.

Additionally, upon achieving the time to effect during any ablation procedure, the graphical display 24 can be configured to display the time it took from beginning of ablation until the targeted cardiac tissue was effectively isolated. Such information relating to time to effect can be included as part of the timing output provided by the timing system 26. Further, in certain embodiments, the cryogenic balloon catheter system 10, e.g., the control console 22 or the control system 14, can include a memory 32 (illustrated as a box in FIG. 1) to store the achieved time to effect for a given ablation procedure, which can be subsequently accessed for further use as desired. The memory 32 can have any suitable design.

Further, based on the specific disclosure provided herein, the control system 14 is able to control the operation of the cryogenic balloon catheter system 10 during an ablation procedure based at least in part on the timing output that is received from the timing system 26 and the sensor output. It is appreciated that the embodiments of the timing system 26 and/or the cryogenic balloon catheter system 10 described in detail herein enable the realization of one or more certain advantages during the cryoablation procedure. For example, with the various designs illustrated and described herein, the timing system 26 and/or the cryogenic balloon catheter system 10 enable the operator to more effectively and accurately monitor the timing of the ablation procedure, and more accurately monitor the time to effect that is reached during the ablation procedure.

It is appreciated that the use of the terms "first" and "second" for the time settings is merely for ease of discussion, and any time settings input by the operator can be referred to as a "first" or "second" time setting. Additionally, in applications in which the operator inputs more than two time settings, e.g., for use during one or more ablation procedures, it is further appreciated that any of the specific time settings can be referred to as a "first", "second", "third", "fourth", etc. time setting.

Figure 2:
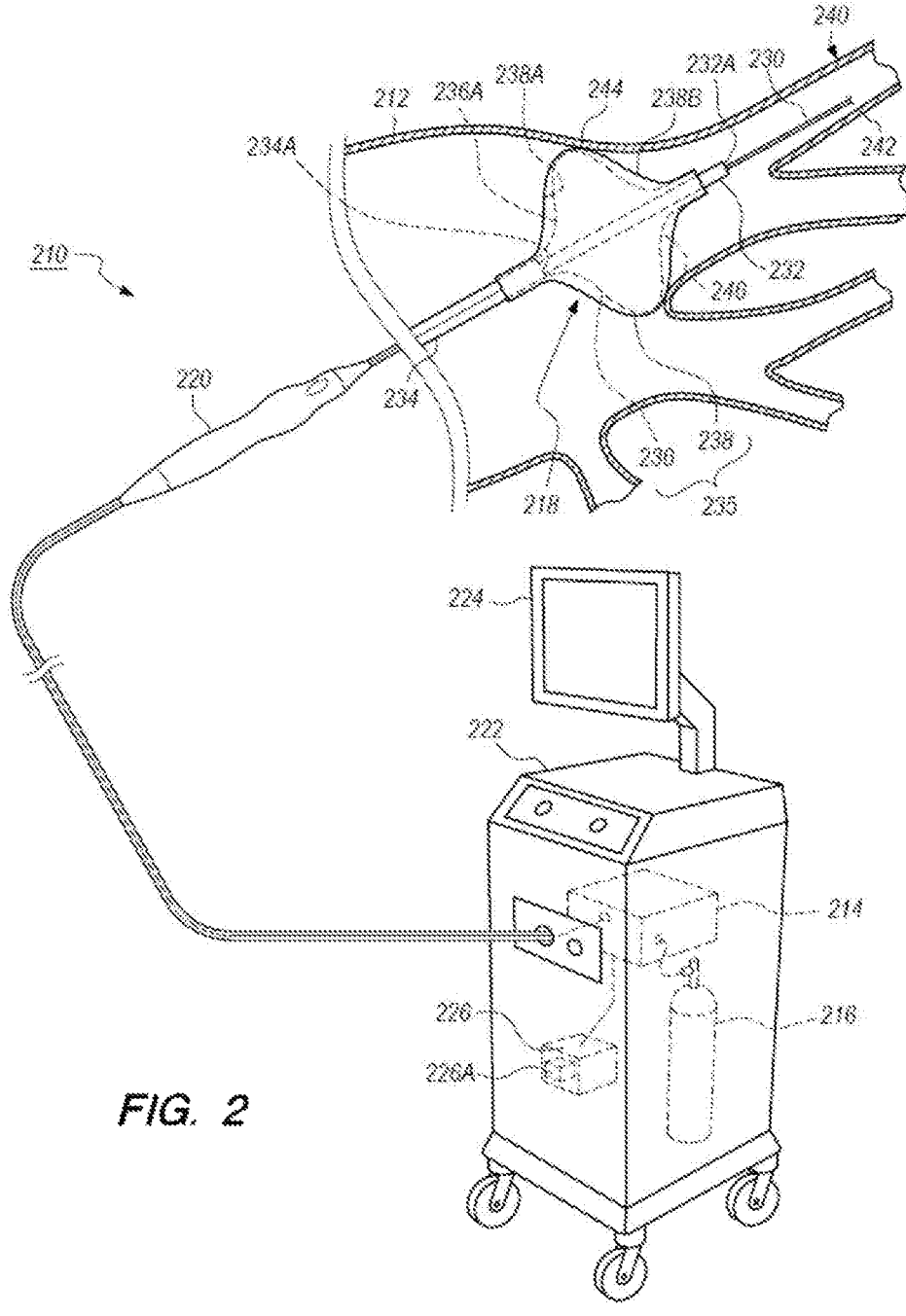
FIG. 2 is a simplified schematic side view illustration of a portion of the patient and a portion of an embodiment of the intravascular catheter system including the timing system.

FIG. 2 is a simplified schematic side view illustration of a portion of one embodiment of the intravascular catheter system 210 and a portion of a patient 212. In the embodiment illustrated in FIG. 2, the intravascular catheter system 210 includes one or more of a control system 214 (illustrated in phantom), a fluid source 216 (illustrated in phantom), a balloon catheter 218, a handle assembly 220, a control console 222, a graphical display 224, and a timing system 226. More particularly, FIG. 2 illustrates various aspects of the balloon catheter 218 in greater detail.

As above, the control system 214 is configured to control various functions of the intravascular catheter system 210. As shown in FIG. 2, in certain embodiments, the control system 214 can be positioned substantially within the control console 222. Alternatively, at least a portion of the control system 214 can be positioned in one or more other locations within the intravascular catheter system 210, e.g., within the handle assembly 220. In various embodiments, the control system 214 can receive the sensor output, the timing output or other output from other components of the intravascular catheter system 210, and can send the sensor output, the timing output, and any other output to the graphical display 224. Further, the control system 214 can control various functions of the remainder of the intravascular catheter system 210 based at least in part on the sensor output, the timing output and/or any other output received by the control system 214.

The design of the balloon catheter 218 can be varied to suit the design requirements of the intravascular catheter system 210. In this embodiment, the balloon catheter 218 includes one or more of a guidewire 230, a guidewire lumen 232, a catheter shaft 234, and a balloon assembly 235 including an inner inflatable balloon 236 (sometimes referred to herein as a "first inflatable balloon", an "inner balloon" or a "first balloon") and an outer inflatable balloon 238 (sometimes referred to herein as a "second inflatable balloon", an "outer balloon" or a "second balloon"). As used herein, it is recognized that either balloon 236, 238 can be described as the first balloon or the second balloon. Alternatively, the balloon catheter 218 can be configured to include only a single balloon. It is also understood that the balloon catheter 218 can include other structures as well. However, for the sake of clarity, these other structures have been omitted from the Figures.

As shown in the embodiment illustrated in FIG. 2, the balloon catheter 218 is configured to be positioned within the circulatory system 240 of the patient 212. The guidewire 230 and guidewire lumen 232 are inserted into a pulmonary vein 242 of the patient 212, and the catheter shaft 234 and the balloons 236, 238 are moved along the guidewire 230 and/or the guidewire lumen 232 to near an ostium 244 of the pulmonary vein 242. In general, it is the object of the balloon catheter 218 to seal the pulmonary vein 242 so that blood flow is occluded. Only when occlusion is achieved does the cryothermic energy, e.g., of the cryogenic fluid 28 (illustrated in FIG. 1), cause tissue necrosis which, in turn, provides for electrically blocking aberrant electrical signals (i.e. electrical isolation) that could otherwise trigger atrial fibrillation.

Additionally, as shown, the guidewire lumen 232 encircles at least a portion of the guidewire 230. During use, the guidewire 230 is inserted into the guidewire lumen 232 and can course through the guidewire lumen 232 and extend out of a distal end 232A of the guidewire lumen 232. In various embodiments, the guidewire 230 can also include a mapping catheter (not shown) that maps electrocardiograms in the heart, and/or can provide information needed to position at least portions of the balloon catheter 218 within the patient 212. In embodiments where the guidewire 230 operates as a mapping catheter, electrodes on the guidewire 230 can operate as electrical sensors capable of providing output signals for use in detecting the time to isolation, as further discussed elsewhere herein.

As illustrated in this embodiment, the inner balloon 236 is positioned substantially, if not completely, within the outer balloon 238. With such design, the outer balloon 238 can protect against the cryogenic fluid 28 leaking out of the balloon assembly 235 should the inner balloon 236 rupture or develop a leak during a cryoablation procedure.

Additionally, in some embodiments, one end of the inner balloon 236 is bonded to a distal end 234A of the catheter shaft 234, and the other end of the inner balloon 236 is bonded near the distal end 232A of the guidewire lumen 232. Further, one end of the outer balloon 238 may be bonded to a neck of the inner balloon 236 or to the distal end 234A of the catheter shaft 234, and the other end of the outer balloon 238 may be bonded to the other end of the inner balloon 236 or to the guidewire lumen 232. Alternatively, the balloons 236, 238 can be secured to other suitable structures. It is appreciated that a variety of bonding techniques can be used and include heat-bonding and adhesive-bonding.

During use, the inner balloon 236 can be partially or fully inflated so that at least a portion of the inner balloon 236 expands toward and/or against at least a portion of the outer balloon 238. Stated in another manner, during use of the balloon catheter 218, at least a portion of an outer surface 236A of the inner balloon 236 expands and can be positioned substantially directly against a portion of an inner surface 238A of the outer balloon 238. As such, when the inner balloon 236 has been fully inflated, the inner balloon 236 and the outer balloon 238 have a somewhat similar physical footprint.

At certain times during usage of the intravascular catheter system 210, the inner balloon 236 and the outer balloon 238 define an inter-balloon space 246, or gap, between the balloons 236, 238. The inter-balloon space 246 is illustrated between the inner balloon 236 and the outer balloon 238 in FIG. 2 for clarity, although it is understood that at certain times during usage of the intravascular catheter system 210, the inter-balloon space 246 has very little or no volume. As provided herein, once the inner balloon 236 is sufficiently inflated, an outer surface 238B of the outer balloon 238 can then be positioned within the circulatory system 240 of the patient 212 to abut and/or substantially form a seal with the ostium 244 of the pulmonary vein 242 to be treated. In particular, during use, it is generally desired that an outer diameter of the balloon assembly 235 be slightly larger than a diameter of the pulmonary vein 242 being treated to best enable occlusion of the pulmonary vein 242. Having a balloon assembly 235 with an outer diameter that is either too small or too large can create problems that inhibit the ability to achieve the desired occlusion of the pulmonary vein 242.

The specific design of and materials used for each of the inner balloon 236 and the outer balloon 238 can be varied. For example, in various embodiments, specialty polymers with engineered properties can be used for forming the inner balloon 236. In such embodiments, two specific families of materials can be especially suitable for use in the inner balloon 236. In particular, some representative materials suitable for the inner balloon 236 include various grades of polyether block amides (PEBA) such as the commercially available PEBAX® (marketed by Arkema, Colombes, France), or a polyurethane such as Pellathane™ (marketed by Lubrizol). Additionally, or in the alternative, the materials can include PET (polyethylene terephthalate), nylon, polyurethane, and other co-polymers of these materials, as non-exclusive examples. In another embodiment, a polyester block copolymer known in the trade as Hytrel® (DuPont™) is also a suitable material for the inner balloon 236. Further, the materials may be mixed in varying amounts to fine tune properties of the inner balloon 236.

Additionally, in certain embodiments, the outer balloon 238 can be formed from similar materials and can be formed in a similar manner as the inner balloon 236. For example, some representative materials suitable for the outer balloon 238 include various grades of polyether block amides (PEBA) such as the commercially available PEBAX®, or a polyurethane such as Pellathane™. Additionally, or in the alternative, the materials can include aliphatic polyether polyurethanes in which carbon atoms are linked in open chains, including paraffins, olefins, and acetylenes. Another suitable material goes by the trade name Tecoflex® (marketed by Lubrizol). Other available polymers from the polyurethane class of thermoplastic polymers with exceptional elongation characteristics are also suitable for use as the outer balloon 238. Further, the materials may be mixed in varying amounts to fine tune properties of the outer balloon 238.

As with the previous embodiment, the timing system 226 provides the operator with a mechanism, i.e. an automated timer 226A, by which the operator can utilize their own specific timing parameters to more easily and precisely control the timing of the various stages of the cryoablation procedure. In certain embodiments, the timing system 226 and/or the automated timer 226A can be electrically connected to the control system 214 and the graphical display 224. As such, any timing output that is provided by the timing system 226 can be used by the control system 214 to control the operation of the various features and components of the intravascular catheter system 210. Additionally, any timing output and any information and data that is based on the timing output can be displayed visually and/or in audio format on the graphical display 224.

Additionally, as above, the timing system 226 and/or the automated timer 226A can be configured to set or control the amount of time that the ablation procedure can be continued before (i.e. as a pre-isolation timer) and/or after (i.e. as a post-isolation timer) the recognition of the time to isolation. Thus, in various embodiments, the operator can selectively input one or more of a first (pre-isolation) time setting and a second (post-isolation) time setting into the timing system 226 for use during an ablation procedure. Further, in certain embodiments, as provided herein, the operator can also input a third time setting so that the automated timer 226A functions as a thaw timer for a designated period of time between ablations; and the operator can also input a fourth time setting so that the automated timer 226A then functions as a post-isolation timer during a second (or subsequent) ablation procedure.

Figure 3:
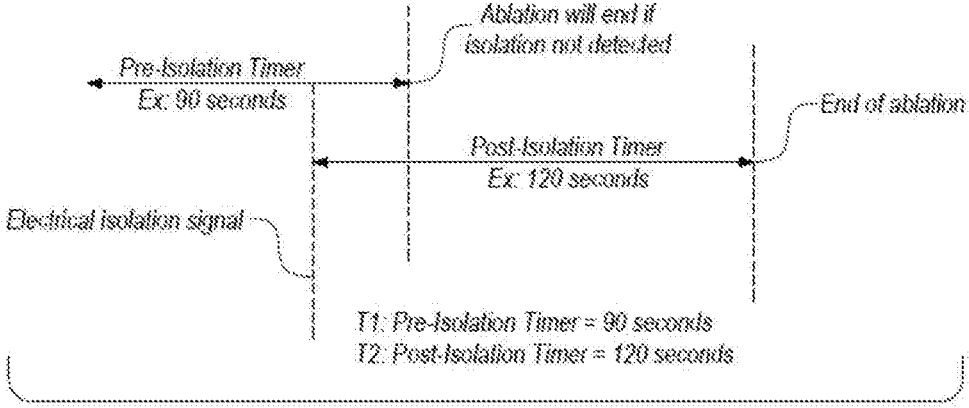
FIG. 3 illustrates a representative example of the timing system being used during an ablation procedure as both a pre-isolation timer and a post-isolation timer.

FIG. 3 illustrates a representative example of the timing system, e.g., the timing system 26 illustrated in FIG. 1 and/or the timing system 226 illustrated in FIG. 2, being used during an ablation procedure as both a pre-isolation timer and a post-isolation timer. In particular, in the example illustrated in FIG. 3, the operator has input a first time setting (T1) so that the automated timer 26A (illustrated in FIG. 1) functions as a pre-isolation timer for a maximum period of ninety seconds; and the operator has input a second time setting (T2) so that the automated timer 26A functions as a post-isolation timer for a period of one hundred twenty seconds.

As shown in FIG. 3, if electrical isolation is not detected by the point of the expiration of the maximum time set for the pre-isolation timer in the first time setting (T1), i.e. by ninety seconds in this example, the control system 14 (illustrated in FIG. 1) will control the intravascular catheter system 10 (illustrated in FIG. 1) to stop the ablation procedure.

However, FIG. 3 also shows that if electrical isolation is detected within the maximum time set for the pre-isolation timer in the first time setting (T1), i.e. before the expiration of ninety seconds, the automated timer 26A will then commence functioning as the post-isolation timer. Subsequently, at the expiration of the time set for the post-isolation timer in the second time setting (T2), i.e. at one hundred twenty seconds, the control system 14 will control the intravascular catheter system 10 to stop the ablation procedure.

Figure 4:
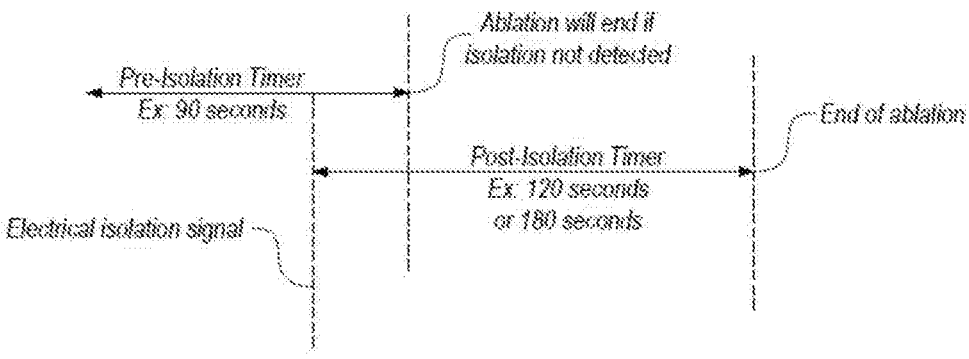
FIG. 4 illustrates another representative example of the timing system being used during an ablation procedure as both a pre-isolation timer and a post-isolation timer.

FIG. 4 illustrates another representative example of the timing system, e.g., the timing system 26 illustrated in FIG. 1 and/or the timing system 226 illustrated in FIG. 2, being used during an ablation procedure as both a pre-isolation timer and a post-isolation timer. In particular, in the example illustrated in FIG. 4, the operator has again input a first time setting (T1) so that the automated timer 26A (illustrated in FIG. 1) functions as a pre-isolation timer for a maximum period of ninety seconds. However, in this example, the operator has input alternative second time settings (T2, T2A) so that the automated timer 26A functions as a post-isolation timer for a period of one hundred twenty seconds or for a period of one hundred eighty seconds, depending on the specific time to isolation that may have been seen during the ablation procedure.

As in the previous example, if electrical isolation is not detected by the point of the expiration of the maximum time set for the pre-isolation timer in the first time setting (T1), i.e. by ninety seconds, the control system 14 (illustrated in FIG. 1) will control the intravascular catheter system 10 (illustrated in FIG. 1) to stop the ablation procedure.

FIG. 4 also shows that if electrical isolation is detected within the maximum time set for the pre-isolation timer in the first time setting (T1), i.e. before the expiration of ninety seconds, the automated timer 26A will then commence functioning as the post-isolation timer. If the time to isolation occurred in a period of less than sixty seconds, the operator has input the second time setting (T2) so that the automated timer 26A functions as the post-isolation timer for a period of one hundred twenty seconds. Subsequently, at the expiration of the time set for the post-isolation timer in the second time setting (T2), i.e. at one hundred twenty seconds, the control system 14 will control the intravascular catheter system 10 to stop the ablation procedure. Alternatively, if the time to isolation occurred in a period of greater than sixty seconds and less than ninety seconds, the operator has input an alternative second time setting (T2A) so that the automated timer 26A functions as the post-isolation timer for a period of one hundred eighty seconds. Subsequently, at the expiration of the time set for the post-isolation timer in the alternative second time setting (T2A), i.e. at one hundred eighty seconds, the control system 14 will control intravascular catheter system 10 to stop the ablation procedure.

Further, in some embodiments, the timing system 26 can also allow the operator to program the timing parameters for consecutive ablation procedures, with a reset thaw time in between the ablation procedures. In such embodiments, the specific timing parameters established by the operator can again be dependent on the realized time to isolation in any of the specific ablation procedures.

Figure 5:
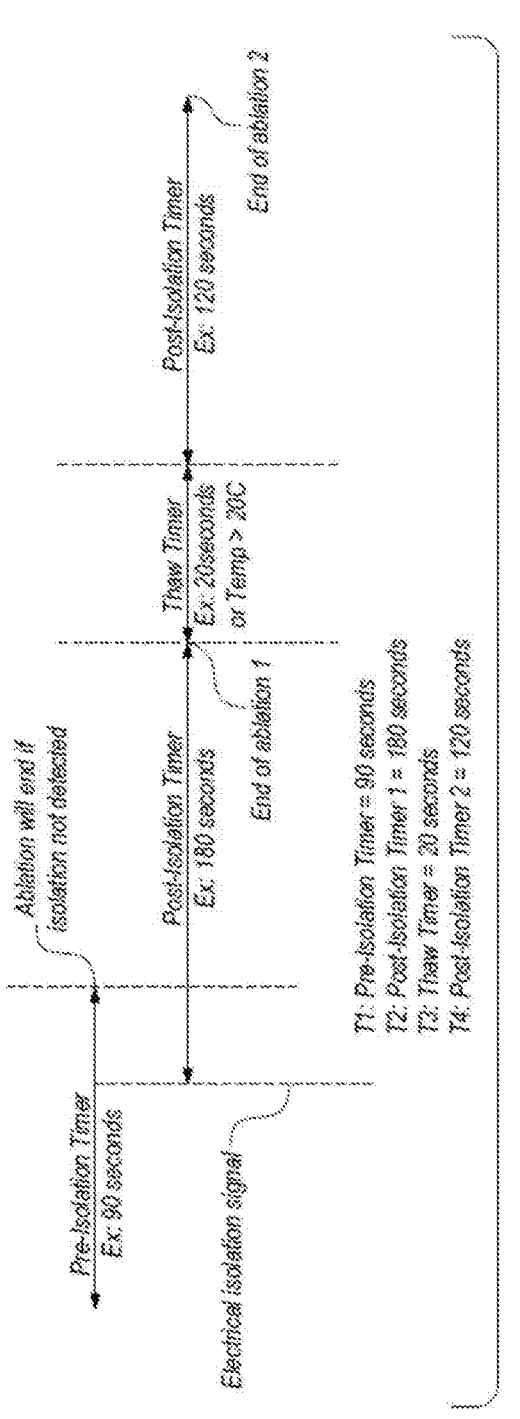
FIG. 5 illustrates a representative example of the timing system being used as both a pre-isolation timer and a post-isolation timer for two consecutive ablation procedures.

FIG. 5 illustrates a representative example of the timing system, e.g., the timing system 26 illustrated in FIG. 1 and/or the timing system 226 illustrated in FIG. 2, being used as both a pre-isolation timer and a post-isolation timer for two consecutive ablation procedures. In particular, in the example illustrated in FIG. 5, the operator has input a first time setting (T1) for an initial ablation procedure so that the automated timer 26A (illustrated in FIG. 1) functions as a pre-isolation timer for a maximum period of ninety seconds; and the operator has input a second time setting (T2) so that the automated timer 26A functions as a post-isolation timer for a period of one hundred eighty seconds. Additionally, in the example illustrated in FIG. 5, the operator has further input a third time setting (T3) so that the automated timer 26A functions as a thaw timer for a period of twenty seconds between ablations; and the operator has also input a fourth time setting (T4) so that the automated timer 26A then functions as a post-isolation timer during the second ablation procedure for a period of one hundred twenty seconds.

As shown in FIG. 5, if electrical isolation is not detected by the point of the expiration of the maximum time set for the pre-isolation timer in the first time setting (T1), i.e. by ninety seconds, the control system 14 (illustrated in FIG. 1) will control the intravascular catheter system 10 (illustrated in FIG. 1) to stop the ablation procedure.

FIG. 5 also shows that if electrical isolation is detected within the maximum time set for the pre-isolation timer in the first time setting (T1), i.e. before the expiration of ninety seconds, the automated timer 26A will then commence functioning as the post-isolation timer. Subsequently, at the expiration of the time set for the post-isolation timer for the initial ablation procedure in the second time setting (T2), i.e. at one hundred eighty seconds, the control system 14 will control the intravascular catheter system 10 to stop the ablation procedure.

Once the initial ablation procedure has been stopped at the end of the one hundred eighty seconds established for the post-isolation timer for the initial ablation procedure in the second time setting (T2), the automated timer 26A commences to function as the thaw timer, i.e. for an established period of twenty seconds in this example. During the thaw period, no ablative energy is being delivered to the tissue. At the expiration of the thaw period as set in the third time setting (T3), the automated timer 26A again beings functioning as the post-isolation timer. Subsequently, at the expiration of the time set for the post-isolation timer for the second ablation procedure in the fourth time setting (T4), i.e. at one hundred twenty seconds, the control system 14 will control the intravascular catheter system 10 to stop the ablation procedure.

Figure 6:
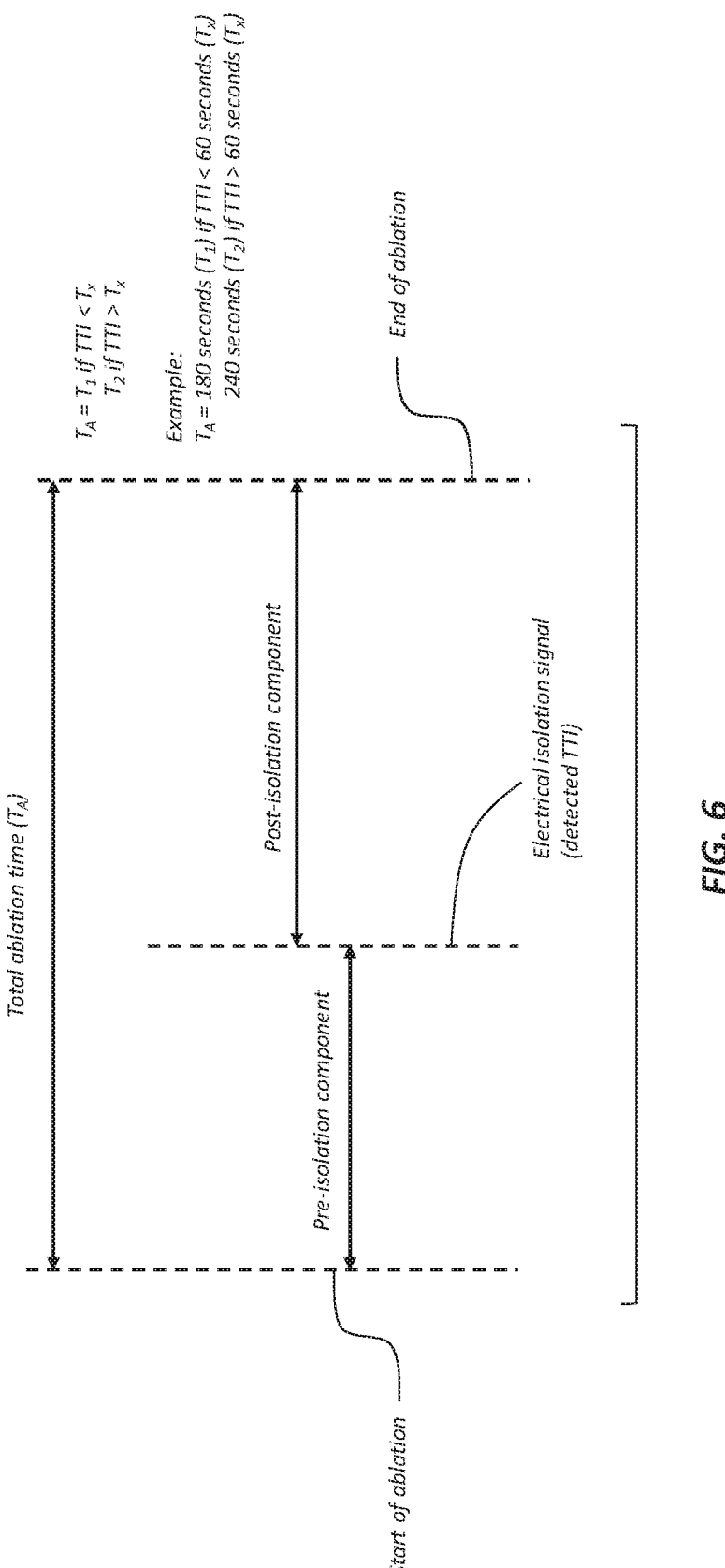
FIG. 6 illustrates a representative example of the timing system of FIGS. 1 and/or 2 according to another embodiment.

FIG. 6 illustrates a representative example of the operation of the timing system, e.g., the timing system 26 illustrated in FIG. 1 and/or the timing system 226 illustrated in FIG. 2, according to another embodiment. In the embodiment of FIG. 6, the automated timer 26A operates as a timer for the entire time period $T_A$ of the overall duration of the application of ablation energy, such that the period $T_A$ has both a pre-isolation component extending from the start of ablation to the detected time to isolation TTI, and post-isolation component extending from the TTI to the end of the ablation phase. In this embodiment, the operator is able to input first and second time settings T1 and T2 for the ablation time $T_A$, and also a TTI setting $T_x$, and the timing system 26 is configured to automatically change the duration of the ablation energy application from T1 to T2 depending on whether the actual detected TTI occurs before (or at) the TTI setting $T_x$, or after the TTI setting $T_x$. Thus, the timing system 26 can effectively extend the overall ablation duration when the actual TTI has not occurred by the time of the TTI setting $T_x$.

In the particular example illustrated in FIG. 6, the operator has defined the TTI setting $T_x$ at 60 seconds, the first ablation time setting T1 at 180 seconds, and the second ablation time setting T2 at 240 seconds. Consequently, if during the ablation procedure, the detected TTI occurs before 60 seconds, the timing system 26 will cause the ablation energy to be applied for 180 seconds. If isolation has not been detected by 60 seconds, however, the timing system will automatically change the overall duration of the application of ablation energy to 240 seconds.

Figure 7:
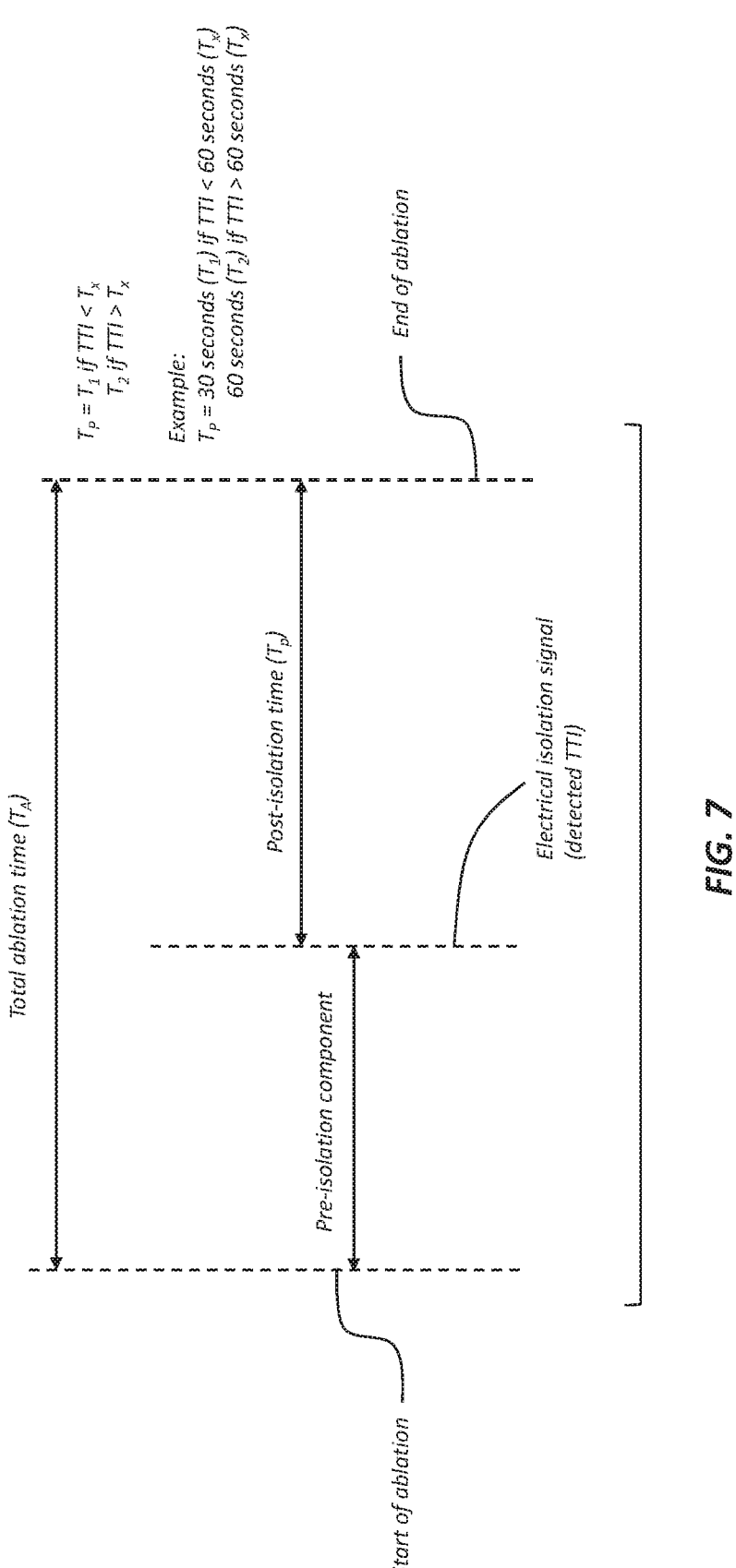
FIG. 7 illustrates a representative example of the timing system of FIGS. 1 and/or 2 according to another embodiment.

FIG. 7 illustrates a representative example of the operation of the timing system, e.g., the timing system 26 illustrated in FIG. 1 and/or the timing system 226 illustrated in FIG. 2, according to another embodiment.

The embodiment of FIG. 7 is in several respects similar to the embodiment of FIG. 6, but differs in that the automated timer 26A operates as a timer for a post-ablation phase of the overall ablation phase. As shown, the duration of the post-isolation phase is represented by the time period $T_P$, and as in FIG. 6, the duration of the overall ablation phase is represented by the time period $T_A$.

In this embodiment, the operator is able to input first and second time settings T1 and T2 for the time of the post-ablation phase $T_P$, and also a TTI setting $T_x$, and the timing system 26 is configured to automatically change the duration of the post-isolation phase from T1 to T2 depending on whether the actual detected TTI occurs before (or at) the TTI setting $T_x$, or after the TTI setting $T_x$. Thus, similar to the embodiment of FIG. 6, the timing system 26 can effectively extend the overall ablation duration when the actual TTI has not occurred by the time of the TTI setting $T_x$ by automatically adjusting the duration of the post-isolation phase as a function of the actual detected TTI.

In the particular example illustrated in FIG. 7, the operator has defined the TTI setting $T_x$ at 60 seconds, the first post-isolation time setting T1 at 30 seconds, and the second post-isolation time setting T2 at 60 seconds. Consequently, if during the ablation procedure, the detected TTI occurs before 60 seconds, the timing system 26 will cause the ablation energy to be applied for an additional 30 seconds. If isolation has not been detected by 60 seconds, however, the timing system will automatically change the duration of the post-isolation application of ablation energy to 60 seconds.

The embodiment of FIG. 6 thus provides an operational advantage of eliminating the need for the clinician to extend the ablation time manually during procedures in which isolation takes longer than initially anticipated.

In various embodiments, the timing system of FIG. 6 can be utilized with the thaw timing configuration described in connection with FIG. 5.

It is understood that the examples shown in FIGS. 3-7 are merely illustrative of representative examples of how the timing system 26 can be utilized within the intravascular catheter system 10. Thus, the application and use of specific timing parameters within such representative examples is not intended to be limiting in any manner.

It is appreciated that the embodiments of the timing system and/or the intravascular catheter system described in detail herein enable the realization of one or more certain advantages during the cryoablation procedure. With the various designs illustrated and described herein, the timing system and/or the intravascular catheter system can more effectively minimize energy delivery to the tissue, as well as effectively minimizing potential collateral tissue damage during the cryoablation procedure.

It is further understood that although a number of different embodiments of the timing system and/or the intravascular catheter system have been illustrated and described herein, one or more features of any one embodiment can be combined with one or more features of one or more of the other embodiments, provided that such combination satisfies the intent of the present invention.

While a number of exemplary aspects and embodiments of the timing system and/or the intravascular catheter system have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A control apparatus for an ablation catheter system for performing an ablation procedure on target cardiac tissue of a patient, the control apparatus comprising a timing system including an automated timer configured to receive, from a user, a first time setting defining a first duration of a post-isolation phase of an ablation phase of the ablation procedure, a second time setting defining a second duration of the post-isolation phase of the ablation phase of the ablation procedure, and a time-to-isolation (TTI) setting, wherein the ablation phase is defined by a start of a delivery of ablation energy and an end of the delivery of ablation energy, and wherein the post-isolation phase of the ablation phase is a portion of the ablation phase following an actual detected TTI, wherein the first time setting is shorter than the second time setting, and wherein the automated timer automatically switches from the first time setting to the second time setting if an actual detected TTI has not occurred prior to the TTI setting.

2. The control apparatus of claim 1, wherein the automated timer is further configured to receive a maximum period of time the ablation phase can continue without reaching the TTI.

3. The control apparatus of claim 2, wherein the first and second time settings each further define a maximum period of time that the ablation phase can continue after reaching the TTI.

4. The control apparatus of claim 1, further comprising a timing activator configured to start the automated timer at the start of ablation and to stop the automated timer at the end of ablation.

5. An ablation catheter system for performing an ablation procedure on target cardiac tissue of a patient, the ablation catheter system comprising:

an ablation catheter;

a control system comprising:

a controller configured to control an ablation phase of the ablation procedure, wherein the ablation phase is defined by a start of ablation and an end of ablation; and a timing system including an automated timer configured to receive, from a user, a first time setting defining a first duration of a post-isolation phase of an ablation phase of the cardiac ablation procedure, a second time setting defining a second duration of the post-isolation phase of the ablation phase of the ablation procedure, and a time-to-isolation (TTI) setting, wherein the ablation phase is defined by a start of a delivery of ablation energy and an end of the delivery of ablation energy, and wherein the post-isolation phase of the ablation phase is a portion of the ablation phase following an actual detected TTI, wherein the first time setting is shorter than the second time setting, and wherein the automated timer automatically switches from the first time setting to the second time setting if an actual detected TTI has not occurred prior to the TTI setting; and a graphical display electrically coupled to the timing system, wherein a user can input the first time setting, the second time setting, and the TTI setting via the graphical display.

6. The ablation catheter system of claim 5, wherein the graphical display is further configured to receive a TTI input from the user upon the user determining that the TTI has occurred.

7. The ablation catheter system of claim 5, further comprising at least one sensor providing an output signal, and wherein the controller is configured to automatically determine whether the TTI has been reached based at least in part on the output signal.

8. The ablation catheter system of claim 5, further comprising a timing activator configured to start the automated timer at the start of ablation and to stop the automated timer at the end of ablation.

* * * * *